United States Patent
Sweeney

(10) Patent No.: US 8,280,508 B2
(45) Date of Patent: *Oct. 2, 2012

(54) SIGNAL COMPRESSION BASED ON CURVATURE PARAMETERS

(75) Inventor: Robert J. Sweeney, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 702 days.

This patent is subject to a terminal disclaimer.

(21) Appl. No.: 12/391,934

(22) Filed: Feb. 24, 2009

(65) Prior Publication Data

US 2009/0192395 A1    Jul. 30, 2009

Related U.S. Application Data

(62) Division of application No. 10/607,820, filed on Jun. 27, 2003, now Pat. No. 7,500,955.

(51) Int. Cl.
*A61N 1/36* (2006.01)
(52) U.S. Cl. .......................................................... 607/9
(58) Field of Classification Search .................. 607/4, 5, 607/9, 14; 600/509, 515–518
See application file for complete search history.

(56) References Cited

U.S. PATENT DOCUMENTS

| 4,336,810 | A | | 6/1982 | Anderson et al. |
|---|---|---|---|---|
| 4,583,553 | A | | 4/1986 | Shah et al. |
| 4,637,400 | A | * | 1/1987 | Marcus ......................... 600/425 |
| 4,721,114 | A | | 1/1988 | DuFault et al. |
| 4,802,491 | A | | 2/1989 | Cohen et al. |
| 4,825,869 | A | | 5/1989 | Sasmor et al. |
| 4,832,038 | A | | 5/1989 | Arai et al. |
| 4,838,278 | A | | 6/1989 | Wang et al. |
| 4,924,875 | A | | 5/1990 | Chamoun |
| 4,947,857 | A | | 8/1990 | Albert et al. |
| 5,014,284 | A | | 5/1991 | Langer et al. |
| 5,046,504 | A | | 9/1991 | Albert et al. |
| 5,184,615 | A | | 2/1993 | Nappholz et al. |
| 5,193,550 | A | | 3/1993 | Duffin |
| 5,201,321 | A | | 4/1993 | Fulton |
| 5,217,021 | A | | 6/1993 | Steinhaus et al. |
| 5,228,438 | A | | 7/1993 | Buchanan |
| 5,240,009 | A | | 8/1993 | Williams |
| 5,271,411 | A | | 12/1993 | Ripley et al. |
| 5,273,049 | A | | 12/1993 | Steinhaus et al. |
| 5,275,621 | A | | 1/1994 | Mehra |
| 5,280,792 | A | | 1/1994 | Leong et al. |
| 5,291,400 | A | | 3/1994 | Gilham |
| 5,292,341 | A | | 3/1994 | Snell |

(Continued)

FOREIGN PATENT DOCUMENTS

DE    4405827    6/1995

(Continued)

OTHER PUBLICATIONS

"U.S. Appl. No. 10/607,820, Response filed Oct. 15, 2008 to Non Final Office Action mailed Jul. 25, 2008", 12 pgs.

(Continued)

*Primary Examiner* — George Evanisko
(74) *Attorney, Agent, or Firm* — Schwegman Lundberg & Woessner, P.A.

(57) ABSTRACT

For a sampled signal, storing characteristic points generated based on parameters corresponding to curvature of the signal. The characteristic points include a time of occurrence of a lobe in a curvature series based on the signal and a corresponding amplitude of the signal. The characteristic points provide a compressed version of the sampled signal. The signal is reconstructed by establishing a function between a chronological sequence of characteristic points. For a repetitive signal, the stored data includes a code to indicate a time of reoccurrence of a previous cycle or data corresponding to differences between a previous cycle and a current cycle.

21 Claims, 8 Drawing Sheets

U.S. PATENT DOCUMENTS

| | | | |
|---|---|---|---|
| 5,292,348 A | 3/1994 | Saumarez et al. | |
| 5,311,874 A | 5/1994 | Baumann et al. | |
| 5,312,445 A | 5/1994 | Nappholz et al. | |
| 5,313,953 A | 5/1994 | Yomtov et al. | |
| 5,330,504 A | 7/1994 | Somerville et al. | |
| 5,331,966 A | 7/1994 | Bennett et al. | |
| 5,334,220 A | 8/1994 | Sholder | |
| 5,342,402 A | 8/1994 | Olson et al. | |
| 5,350,406 A | 9/1994 | Nitzsche et al. | |
| 5,351,696 A | 10/1994 | Riff et al. | |
| 5,360,436 A | 11/1994 | Alt et al. | |
| 5,365,934 A | 11/1994 | Leon et al. | |
| 5,366,487 A | 11/1994 | Adams et al. | |
| 5,383,910 A | 1/1995 | den Dulk | |
| 5,387,229 A | 2/1995 | Poore | |
| 5,391,189 A | 2/1995 | van Krieken et al. | |
| 5,400,795 A | 3/1995 | Murphy et al. | |
| 5,411,031 A | 5/1995 | Yomtov | |
| 5,417,714 A | 5/1995 | Levine et al. | |
| 5,431,693 A | 7/1995 | Schroeppel | |
| 5,447,519 A | 9/1995 | Peterson | |
| 5,458,620 A | 10/1995 | Adams et al. | |
| 5,464,433 A | 11/1995 | White et al. | |
| 5,480,412 A | 1/1996 | Mouchawar et al. | |
| 5,487,754 A | 1/1996 | Snell et al. | |
| 5,503,159 A | 4/1996 | Burton | |
| 5,511,554 A | 4/1996 | Helfenbein et al. | |
| 5,513,644 A | 5/1996 | McClure et al. | |
| 5,514,163 A | 5/1996 | Markowitz et al. | |
| 5,520,191 A | 5/1996 | Karlsson et al. | |
| 5,542,430 A | 8/1996 | Farrugia et al. | |
| 5,545,186 A | 8/1996 | Olson et al. | |
| 5,549,641 A | 8/1996 | Ayers et al. | |
| 5,560,369 A | 10/1996 | McClure et al. | |
| 5,603,331 A | 2/1997 | Heemels et al. | |
| 5,605,159 A | 2/1997 | Smith et al. | |
| 5,628,326 A | 5/1997 | Arand et al. | |
| 5,645,070 A | 7/1997 | Turcott | |
| 5,676,153 A | 10/1997 | Smith et al. | |
| 5,682,900 A | 11/1997 | Arand et al. | |
| 5,685,315 A | 11/1997 | McClure et al. | |
| 5,697,959 A | 12/1997 | Poore | |
| 5,704,365 A | 1/1998 | Albrecht et al. | |
| 5,712,801 A | 1/1998 | Turcott | |
| 5,713,367 A | 2/1998 | Arnold et al. | |
| 5,718,242 A | 2/1998 | McClure et al. | |
| 5,730,142 A | 3/1998 | Sun et al. | |
| 5,738,105 A | 4/1998 | Kroll | |
| 5,749,900 A | 5/1998 | Schroeppel et al. | |
| 5,755,739 A | 5/1998 | Sun et al. | |
| 5,778,881 A | 7/1998 | Sun et al. | |
| 5,779,645 A * | 7/1998 | Olson et al. | 600/518 |
| 5,782,888 A | 7/1998 | Sun et al. | |
| 5,788,717 A | 8/1998 | Mann et al. | |
| 5,792,065 A | 8/1998 | Xue et al. | |
| 5,792,066 A | 8/1998 | Kwong | |
| 5,795,303 A | 8/1998 | Swanson et al. | |
| 5,797,399 A | 8/1998 | Morris et al. | |
| 5,810,739 A | 9/1998 | Bornzin et al. | |
| 5,814,077 A | 9/1998 | Sholder et al. | |
| 5,817,133 A | 10/1998 | Houben | |
| 5,819,007 A | 10/1998 | Elghazzawi | |
| 5,819,741 A | 10/1998 | Karlsson et al. | |
| 5,827,195 A | 10/1998 | Lander | |
| 5,836,889 A | 11/1998 | Wyborny et al. | |
| 5,836,987 A | 11/1998 | Baumann et al. | |
| 5,855,593 A | 1/1999 | Olson et al. | |
| 5,858,977 A | 1/1999 | Aukerman et al. | |
| 5,868,680 A | 2/1999 | Steiner et al. | |
| 5,873,897 A | 2/1999 | Armstrong et al. | |
| 5,873,898 A | 2/1999 | Hemming et al. | |
| 5,935,082 A | 8/1999 | Albrecht et al. | |
| 5,941,831 A | 8/1999 | Turcott | |
| 5,944,744 A | 8/1999 | Paul et al. | |
| 5,951,592 A | 9/1999 | Murphy | |
| 5,954,661 A | 9/1999 | Greenspon et al. | |
| 5,978,700 A | 11/1999 | Nigam | |
| 5,978,707 A | 11/1999 | Krig et al. | |
| 5,983,138 A | 11/1999 | Kramer | |
| 5,991,656 A | 11/1999 | Olson et al. | |
| 5,991,657 A | 11/1999 | Kim | |
| 6,016,442 A | 1/2000 | Hsu et al. | |
| 6,024,705 A | 2/2000 | Schlager et al. | |
| 6,049,735 A | 4/2000 | Hartley et al. | |
| 6,052,617 A | 4/2000 | Kim | |
| 6,076,014 A | 6/2000 | Alt | |
| 6,081,745 A | 6/2000 | Mehra | |
| 6,091,990 A | 7/2000 | Hsu et al. | |
| 6,192,273 B1 | 2/2001 | Igel et al. | |
| 6,212,428 B1 | 4/2001 | Hsu et al. | |
| 6,233,078 B1 | 5/2001 | Harano et al. | |
| 6,233,487 B1 | 5/2001 | Mika et al. | |
| 6,253,102 B1 | 6/2001 | Hsu et al. | |
| 6,263,242 B1 | 7/2001 | Mika et al. | |
| 6,266,554 B1 | 7/2001 | Hsu et al. | |
| 6,272,377 B1 | 8/2001 | Sweeney et al. | |
| 6,275,732 B1 | 8/2001 | Hsu et al. | |
| 6,301,499 B1 | 10/2001 | Carlson et al. | |
| 6,301,503 B1 | 10/2001 | Hsu et al. | |
| 6,308,095 B1 | 10/2001 | Hsu et al. | |
| 6,312,388 B1 | 11/2001 | Marcovecchio et al. | |
| 6,370,430 B1 | 4/2002 | Mika et al. | |
| 6,400,982 B2 | 6/2002 | Sweeney et al. | |
| 6,430,435 B1 | 8/2002 | Hsu et al. | |
| 6,430,438 B1 | 8/2002 | Chen et al. | |
| 6,434,417 B1 | 8/2002 | Lovett | |
| 6,438,410 B2 | 8/2002 | Hsu et al. | |
| 6,449,503 B1 | 9/2002 | Hsu | |
| 6,470,210 B1 | 10/2002 | Chen et al. | |
| 6,484,055 B1 | 11/2002 | Marcovecchio | |
| 6,516,219 B1 | 2/2003 | Street | |
| 6,516,225 B1 | 2/2003 | Florio | |
| 6,539,257 B1 | 3/2003 | KenKnight | |
| 6,571,121 B2 | 5/2003 | Schroeppel et al. | |
| 6,684,100 B1 | 1/2004 | Sweeney et al. | |
| 6,950,702 B2 | 9/2005 | Sweeney | |
| 7,500,955 B2 * | 3/2009 | Sweeney | 600/508 |
| 7,792,571 B2 * | 9/2010 | Sweeney et al. | 600/509 |
| 2002/0193696 A1 | 12/2002 | Hsu et al. | |
| 2004/0010200 A1 | 1/2004 | Sweeny et al. | |
| 2004/0127806 A1 | 7/2004 | Sweeney | |
| 2005/0159781 A1 | 7/2005 | Hsu et al. | |

FOREIGN PATENT DOCUMENTS

| | | |
|---|---|---|
| EP | 469817 A2 | 7/1991 |
| EP | 506230 A1 | 2/1992 |
| WO | WO-97/39681 A1 | 10/1997 |
| WO | WO-99/65570 A1 | 12/1999 |
| WO | WO-00/10455 A1 | 3/2000 |
| WO | WO-00/47278 A1 | 8/2000 |
| WO | WO-01/41870 A2 | 6/2001 |
| WO | WO-02/40094 A2 | 5/2002 |
| WO | WO-2005/002669 A2 | 1/2005 |

OTHER PUBLICATIONS

"U.S. Appl. No. 10/607,820, Amendment and Response filed Apr. 19, 2007 to Non-Final Office Action mailed Nov. 22, 2006", 15 pgs.

"U.S. Appl. No. 10/607,820, Non-Final Office Action mailed Jul. 25, 2008", 4 pgs.

"U.S. Appl. No. 10/607,820, Non-Final Office Action mailed Nov. 22, 2006", 9 pgs.

"International Search Report for PCT Application No. PCT/US2004/020723", (Feb. 10, 2005), 7 pgs.

"Written Opinion for PCT Application No. PCT/US2004/020723", (Feb. 10, 2005), 12 pgs.

Sweeney, Robert J., "Tachyarrhythmia Detection and Discrimination Based on Curvature Parameters", U.S. Appl. No. 10/607,818, filed Jun. 27, 2003, 59 pgs.

Vapnik, V. N., "Chapter 5 Constructing Learning Algorithms", *The Nature of Statistical Learning Theory*, Springer-Verlag New York, Inc., (1995), 119-166.

* cited by examiner

SIGNAL COMPRESSION BASED ON CURVATURE PARAMETERS

CROSS REFERENCE TO RELATED APPLICATIONS

This application is a divisional of U.S. application Ser. No. 10/607,820, filed Jun. 27, 2003, now issued as U.S. Pat. No. 7,500,955, which is hereby incorporated by reference in its entirety.

This document is related to co-pending and commonly assigned U.S. patent application Ser. No. 10/607,818, entitled TACHYARRHYTEIMIA DETECTION AND DISCRIMINATION BASED ON CURVATURE PARAMETERS," inventor Sweeney et al., filed on Jun. 27, 2003, now issued as U.S. Pat. No. 7,792,571, the specification of which is hereby incorporated by reference in its entirety.

This document is related to co-pending and commonly assigned U.S. patent application Ser. No. 10/195,838, entitled "USE OF CURVATURE BASED FEATURES FOR BEAT DETECTION," inventor Sweeney, filed on Jul. 15, 2002, now U.S. Pat. No. 6,950,702, the specification of which is hereby incorporated by reference in its entirety.

This document is related to co-pending and commonly assigned U.S. patent application Ser. No. 10/607,818, entitled TACHYARRHYTHMIA DETECTION AND DISCRIMINATION BASED ON CURVATURE PARAMETERS," inventor Sweeney et al., filed on Jun. 27, 2003, the specification of which is hereby incorporated by reference in its entirety.

TECHNICAL FIELD

This document relates generally to signal compression and particularly, but not by way of limitation, to electrocardiogram signal storage in an implantable medical device.

BACKGROUND

Implantable cardiac rhythm management devices typically monitor and process cardiac signals to provide therapy to the heart. Therapy may include delivering a pacing pulse to trigger a contraction of the heart or delivering a defibrillation shock to interrupt an abnormal heart rhythm. Some cardiac rhythm management devices also monitor cardiac performance or other physiological parameters for use in controlling the delivery of pacing pulses.

There exists an unmet need for providing improved data storage systems, devices, and methods to provide better diagnosis or treatment of patients.

SUMMARY

The present subject matter provides a curvature based method of selecting features from a sampled signal. In one embodiment, the sampled signal includes a cardiac signal or an electrocardiogram. According to one aspect of the present subject matter, characteristic points are selected by sensing a cardiac signal on a real-time basis and upon receipt of each sample, computing curvatures on a continuous basis. Characteristic points are sometimes referred to as significant points or data points.

In one embodiment, each "turn" in the signal is represented with a characteristic point that has measures of time, value, area and width. Time refers to a time denoting the center of the turn in the curvature series. Value refers to the amplitude of the input signal at the time of the center of the turn. Area refers to a value denoting the direction and degree of the turn. Width refers to a value denoting the duration over which the turn occurs.

In one embodiment, the area is described as the angle taken by the signal between the start of a turn and the end of a turn where the turn defines a lobe. The area, in one embodiment, is expressed in radians.

By the methods presented herein, each new characteristic point is known as soon as the turn which it describes has ended. In one embodiment, the stream of characteristic points are analyzed continuously as each new characteristic point occurs. In one embodiment, the characteristic points are saved into a buffer for analysis at a later time.

All turns in an input signal are not the same. Some turns may be large deflections with sharp angles (for example, turns in a QRS signal) while other turns might be slight and not associated with big deflections (for example, noise in the signal). In one embodiment, the present subject matter includes a scheme to select prominent characteristic points in a signal and discard the smaller ones that may represent noise or only slight signal deflections.

The area for the characteristic point is an indirect measure of the angular turn in the signal. The maximum turn is approximately 180 degrees which represents a very rapid signal reversal. A large deflection in the signal, such as the R-wave (a full signal swing in 10 samples over, a period of 50 ms) would have large turn angle of 178 degrees. A small noise spike (such as a 10% full scale swing for a single sample) may also have a large turn angle of 175 degrees. The present subject matter treats these signal deflections differently. The R-wave has a large area whereas the noise spike would have a small area since it occurred over a lower number of samples. Thus, the characteristic point area is a surrogate for determining which characteristic points are important and which are not.

The effect of the foregoing is that small characteristic points at or near the signal baseline value are ignored. According to one embodiment, an absolute area threshold value in the range of 0.5 is used for a rate-sensing channel.

In one embodiment, the present subject matter automatically adjusts the threshold value to better adapt to varying patients and signals.

In one embodiment, each characteristic point includes a time component, an amplitude component and an area component. According to the present subject matter, the time, amplitude and area components are derived from a curvature calculation performed using the sampled signal.

In one embodiment, the plurality of characteristic points are stored in lieu of the sampled signal. By storing characteristic points rather than the sampled signal, the memory required for a particular duration of a sampled signal is reduced, or compressed. Further compression of the data is achieved, in one embodiment, by storing a repetition marker denoting that a group, or cluster, of characteristic points is substantially a duplicate of another cluster of characteristic points. Each cluster, for example, can represent a particular morphological feature such as a heart beat. A timing code is stored with the repetition marker to denote when the cluster occurred. In one embodiment, a difference marker is stored to indicate that a cluster of characteristic points differs from another cluster of characteristic points. A difference code is stored with the difference marker to denote differences between the particular cluster and a previously stored cluster of characteristic points. As with the repetition marker, a timing code is stored with the difference marker to denote when the particular cluster occurred.

In one embodiment, only characteristic points having an absolute value of an area larger than a predetermined threshold are stored. Characteristic points having an absolute value of the area less than the threshold value are discarded or ignored.

In one embodiment, the sampled signal is reconstructed from the stored characteristic points by establishing a function between sequential characteristic points. In various embodiments, the function includes a straight line, a polynomial fit, a parabolic fit, a cubic spline or other function.

Other aspects of the invention will be apparent on reading the following detailed description of the invention and viewing the drawings that form a part thereof.

BRIEF DESCRIPTION OF THE DRAWINGS

In the drawings, like numerals describe substantially similar components throughout the several views. Like numerals having different letter suffixes represent different instances of substantially similar components.

DETAILED DESCRIPTION

In the following detailed description, reference is made to the accompanying drawings that form a part hereof, and in which is shown, by way of illustration, specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present subject matter. The following detailed description is, therefore, not to be taken in a limiting sense, and the scope of the present invention is defined by the appended claims and their equivalents.

This document discloses, among other things, systems, method and apparatus involving cardiac rhythm management systems used for sensing a cardiac signal, including intracardiac electrogram or surface electrocardiogram (ECG). Such cardiac rhythm management systems include, but are not limited to, pacemakers, CRT devices, cardioverter/defibrillators, pacer/defibrillators, and drug delivery devices. However, it is to be understood that the present methods and apparatuses of compressing a signal can be applied to heart beat detection as well as other signals related to cardiac activities, including, but not being limited to, mechanical motion, sound, pressure, acceleration, and impedance signals.

Curvature-Based Analysis

Figure 1:
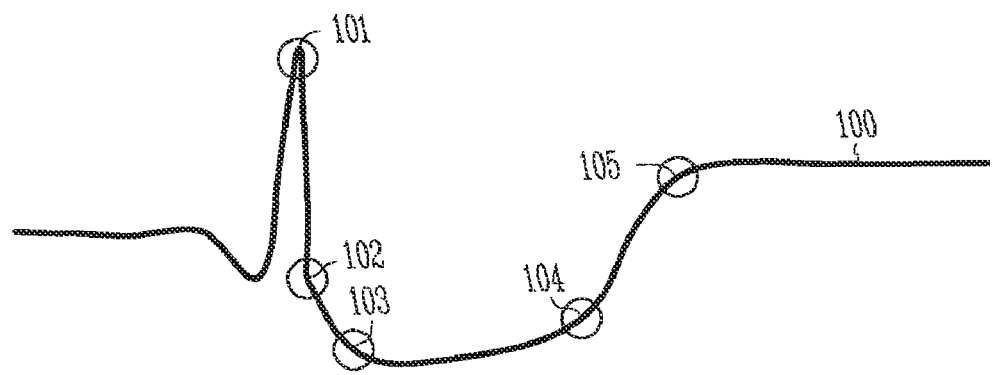
FIG. 1 illustrates an arbitrary signal as a function of time.

For an arbitrary voltage versus time signal, the salient characteristics can be captured in terms of those points along the signal where it makes characteristic "turns." In general, these points are different from those that would be selected using first or second derivative criteria as shown in FIG. 1. In the figure, which illustrates arbitrary electrogram 100, the R wave, denoted as point 101, has a high second derivative $d^2V/dt^2$. Further, the electrogram sections on either side of point 101 have high positive and negative slopes detectable with a first derivative criteria. However, those points with these large (or even maximum) slopes do not convey any particularly significant description of the electrogram. For example, at each time along a segment between points 101 and 102, the waveform has a large negative slope but no point along this segment stands out significantly from any other.

On the other hand, points 102, 103, 104 and 105 are neither maximums nor minimums of the electrogram or its derivatives. These points are descriptive of the arbitrary waveform shape. Points 102, 103, 104 and 105 are salient because they mark locations where the signal makes significant turns. The turn at point 101 is very sharp and the turns at points 103 and 105 are less sharp turns and more broad. The turns at points 102 and 104 are even less sharp but rather local. The present subject matter detects points 101, 102, 103, 104 and 105 using a criteria based on the curvature of the signal.

Figure 2:
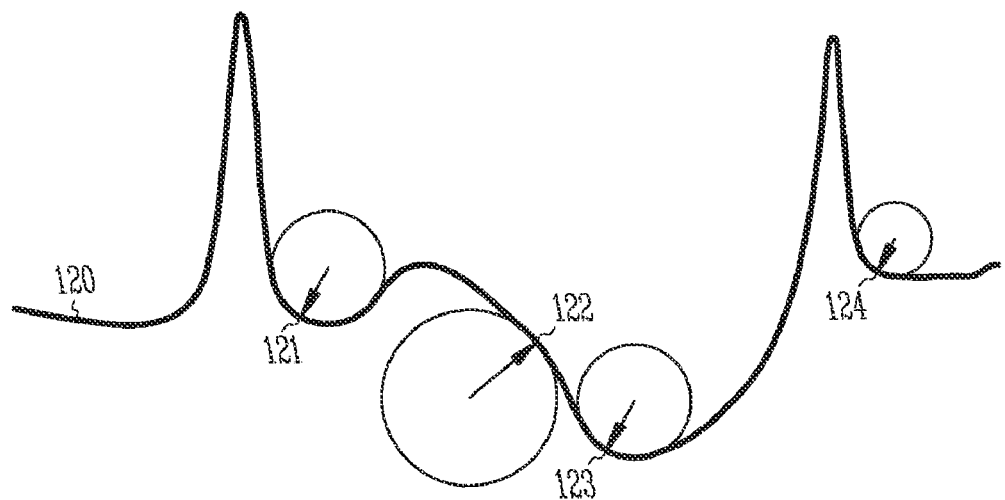
FIG. 2 illustrates osculating circles fitted to an arbitrary signal as a function of time.

According to one embodiment of the present subject matter, signal curvature is illustrated in FIG. 2. In the figure, arbitrary electrogram 120 is shown. At each point along electrogram 120, an osculating circle can be found that fits tangentially with the local portion of the electrogram. Each circle has a radius. The curvature of electrogram 120 at that point is the inverse of that radius so that small circles have large curvatures while large circles have small curvature. FIG. 2 shows these circles at selected points. At point 122, the circle is larger, and thus the curvature is smaller, than at points 121, 123 and 124. At points 121, 123 and 124, the turns are sharper and the curvature is larger.

In general, the curvature at point (X, Y) of an arbitrary curve in a two-dimensional space is expressed as:

$$\text{Curvature} = \frac{d^2Y/dX^2}{[1 + \{dY/dX\}^2]^{3/2}}.$$

As seen, the curvature is a non-linear combination of both the first and second derivatives of the curve. At those points along the curve where the first derivative is zero (for example, point 101 in FIG. 1), the curvature is equal to the second derivative and at points where the second derivative is zero (for example, any straight section regardless of its slope), the curvature is zero.

The present subject matter calculates curvature of an arbitrary input signal on a sample-by-sample basis.

Consider the question of dimensionality of the curvature for electrogram signals. When both X and Y have the same dimensions (say length) then curvature has a dimension of 1/length. For an arbitrary signal having a voltage as a function of time V(t), such as an electrocardiogram, the signal is transformed into a time-versus-time signal T(t) according to T(t)=V(t)/U where U is a constant with dimensions of voltage/time. With this transformation, the first and second derivatives of T(t) become $$\frac{dT}{dt}(t) = \frac{dV}{dt}(t) \cdot 1/U$$

which is dimensionless and $$\frac{d^2 T}{dt^2}(t) = \frac{d^2 V}{dt^2}(t) \cdot 1/U$$

which has dimensions of 1/time and thus the curvature has dimensions of 1/time. Curvature is then expressed as:

$$\text{Curvature} = \frac{d^2 T(t)/dt^2}{[1 + \{dT(t)/dt\}^2]^{3/2}} = \frac{d^2 V(t)/dt^2/U}{[1 + \{dV(t)/dt/U\}^2]^{3/2}}$$

which has dimensions of 1/time and U has a numerical value.

Consider next, curvature as a function of signal gain or amplitude of the input signal. Assume arbitrary gain G is applied to the input signal to find a new input signal F(t) wherein F(t)=G·T(t)=V(t)·G/U. The curvature of the gained signal is then:

$$\text{Curvature} = \frac{d^2 F(t)/dt^2}{[1 + \{dF(t)/dt\}^2]^{3/2}} = \frac{d^2 V(t)/dt^2 \cdot G/U}{[1 + \{dV(t)/dt \cdot G/U\}^2]^{3/2}}.$$

Since the selection of the gain applies to all point in the input signal, the gain G can be thought of as a value that emphasizes the curvature at different points along the signal. For a given V(t), a small value for G will emphasize the curvature at those points on V(t) where dV(t)/dt is large and will de-emphasize the curvature at those points where dV(t)/dt is small. Large values for G have the opposite effect.

The ratio G/U can be expressed as W having dimensions of time/voltage. In one embodiment, the input signal is a voltage sampled with a 12-bit analog-to-digital converter (ADC) having numerical voltage values in the range+/−2048 where each value represents a number of basic amplitude units ΔV, or voltage resolution. It is assumed that the amplifiers in the present subject matter are adjusted so that the samples from V(t) largely fill this range. Furthermore, it is assumed that the samples are taken at a fixed rate and thus the time is represented by an integer number of samples with each sample representing a time interval ΔT=time resolution=1/(sample rate).

Figure 3:
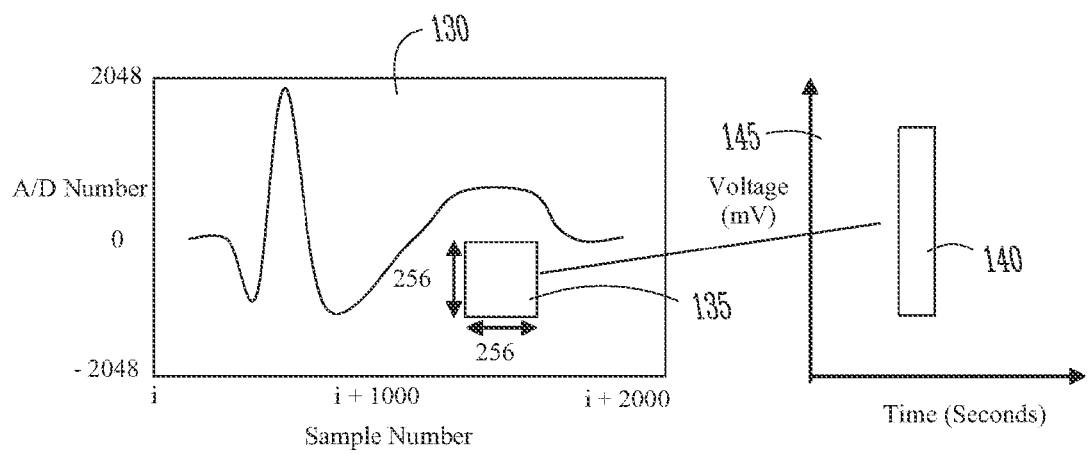
FIG. 3 illustrates a signal expressed in analog-to-digital converter value as a function of sample number.

FIG. 3 illustrates numerical X-Y space 130 which is denoted by sample numbers on the X-axis and the analog-to-digital conversion value on the Y-axis. Consider square 135 in X-Y space 130 which is 256 steps along the X-axis and 256 steps along the Y-axis and rectangle 140 in voltage-time space 145 that this square represents. Rectangle 140 has a width of 256/(sample rate), in seconds and a height of 256/(voltage resolution), in volts. Depending on the values selected for ΔV and ΔT, this rectangle may or may not be a square in voltage-time space.

In one embodiment, W is selected to require that a square in voltage-time space be represented by a square in sample-sample space. Under that condition, the curvature versus time relationships that exist in voltage-time space are preserved in sample-sample space.

Figure 4:
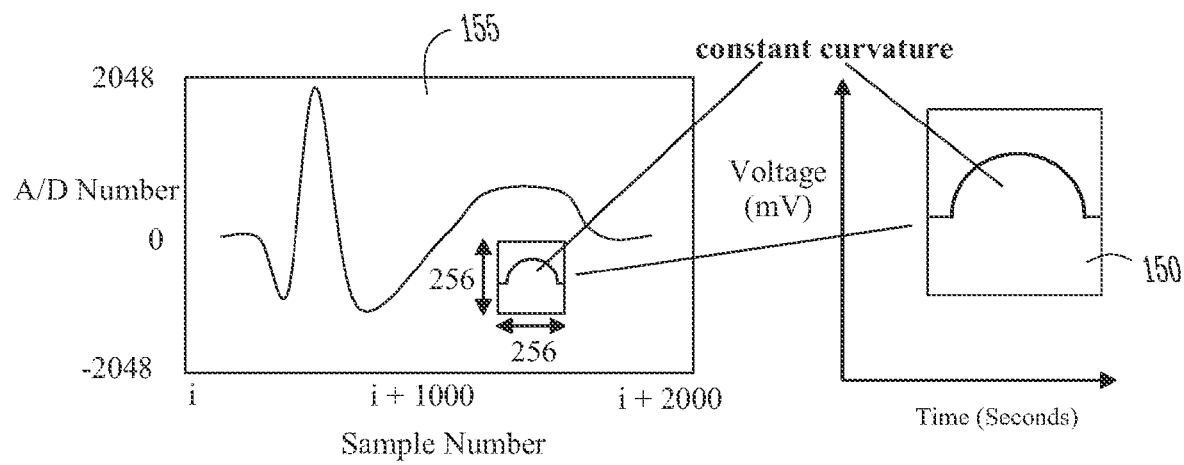
FIG. 4 illustrates a signal expressed in analog-to-digital converter value as a function of sample number and having a constant curvature.

In FIG. 4, an artificial voltage-time curve is shown that forms a semicircle inside square box 150. Traversing from left to right across box 150 in voltage time space, the curvature of the signal is zero until the semicircle is encountered. The curvature jumps to a constant value, equal to 1/radius of the circle, and again jumps to zero at the end of the semicircle. For a particular value of W, the representation of this signal in sample-sample space 155 also has a constant curvature and for other values of W, the curvature would not be constant in sample-sample space.

To maintain this relationship between voltage-time and sample-sample space, W is selected as follows. In voltage-time space, the box T wide by V high is taken to be square. In sample-sample space, the box is T/ΔT time-samples wide and GV/ΔV voltage-samples high and through a transformation, the voltage sample is converted into time-samples using U so that the sample-space square has dimensions of TΔT by VG/ΔV/U. For the box to be square in sample-space, and assuming the box (V by T) in voltage-time space is square, then (V/ΔV)·G/U=T/ΔT or G/U=W=(TΔT)/(V/ΔV).

According to one embodiment of the present subject matter, curvature is based on the first and second derivative of the signal. A least square cubic polynomial fit is used to reduce the noise that would otherwise result from using numerical estimates for the derivatives and using non-linear calculations to find curvature.

The sampled voltage signal is expressed as V(t)=V(I·ΔT) where t=i·ΔT so that the fit of size N uses 2N+1 voltage samples centered on the time t, thus:

V([i−n]·ΔT), . . . V([i−2]·ΔT),V([i−1]·ΔT),V(i·ΔT),
V([i+1]·ΔT),V([i+2]·ΔT), . . . V ([i+n]·ΔT).

This set of N sampled data points is used to make the least-squares cubic fit which is given as $V_{est}$[i·ΔT+dt]=Ai+Bi·[dt]+Ci·[dt]²+Di·[dt]³ where Ai, Bi, Ci, and Di are coefficients determined by minimizing the square error for the fit and dt represents a time step away from i·ΔT at which $V_{est}$ is evaluated. The coefficients in the polynomial are denoted with an i to indicate that they are valid for the point i ΔT.

Using the above equations, the curvature on a point to point basis, at the time i·ΔT, becomes $$\text{Curvature}(i \cdot \Delta T) = \frac{d^2 V(t)/dt^2 \cdot W}{[1 + \{dV(t)/dt \cdot W\}^2]^{3/2}} = \frac{2 \cdot Ci \cdot W}{[1 + \{Bi \cdot W\}^2]^{3/2}}.$$

Sample points, however, will not necessarily fall at the times where the signal curvature has a maximum or minimum value. Thus, in one embodiment, the curvature signal is integrated between adjacent sample points using estimates for the first and second derivative of the signal at the sample points.

Further simplification yields an expression for average point curvature as:

$$Cavg_i = \frac{1}{(B_i - B_{i-1})^2} \cdot \left\{ \frac{C_{i-1} \cdot B_1^2 - C_i \cdot B_i \cdot B_{i-1} - C_i + C_{i-1}}{(B_i^2 + 1)^{1/2}} + \frac{C_i \cdot B_{i-1}^2 - C_{i-1} \cdot B_{i-1} \cdot B_i + C_i - C_{i-1}}{(B_{i-1}^2 + 1)^{1/2}} \right\},$$

$$B_i \neq B_{i-1}$$

$$Cavg_i = \frac{1}{2} \cdot \frac{C_i + C_{i-1}}{(B_i^2 + 1)^{3/2}}, B_i = B_{i-1}.$$

As noted, curvature is computed on a sample-by-sample basis from the input signal.

Consider next, a procedure for finding the characteristic points in the signal.

Figure 5:
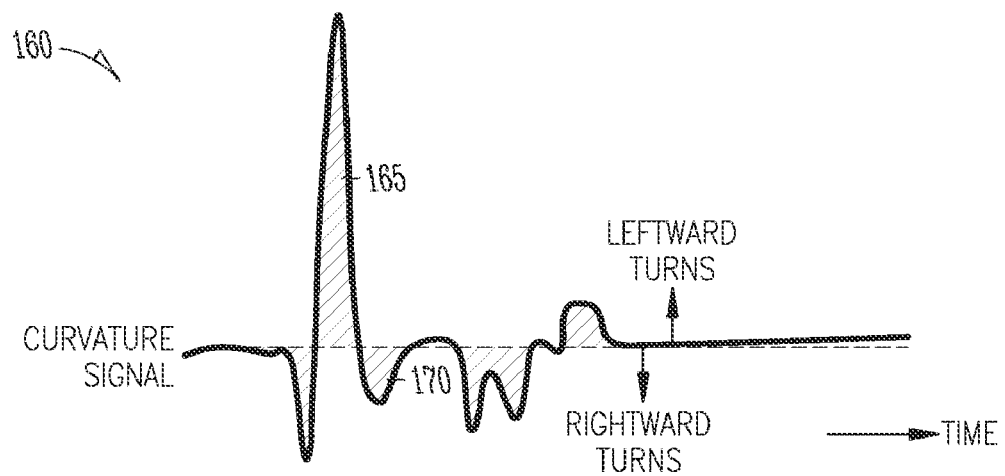
FIG. 5 illustrates characteristic points based on curvature as a function of time.

Turns in the original signal are reflected as excursions above and below zero in the curvature signal. As suggested by curvature 160 of FIG. 5, each lobe above zero (for example, lobe 165) or below zero (for example, lobe 170) then represents a single turn in the input signal. Positive curvature lobes represent a leftward turn and negative curvature lobes represent a rightward turn. The area under each lobe is the total angle included in the turn.

A point-by-point method is used to identify the lobes as they occur and to find the area and centroid of each lobe.

Curvature values are generated on a sample by sample basis. At each sample time, CRV represents the current curvature value and $CRV_{old}$ represents the previous value that is retained from the previous sample. When the curvature value is zero, the original signal is not turning so that no characteristic points may exist. The value CRV will rarely be exactly equal to zero.

In one embodiment, a dead-zone surrounding zero is defined where the calculated curvature may be treated as equal to zero. For times where the curvature is within the zone, the signal is not changing significantly. The zone is defined with a single curvature threshold value that extends above and below zero from $+CRV_{thresh}$ to $-CRV_{thresh}$.

In one embodiment, the present subject matter identifies nine cases for considering the value of CRV relative to the threshold and the absence or direction of a lobe. These cases can be described as follows:

Case 1: $CRV > CRV_{thresh}$ and not in a Lobe.

Here, the current curvature value is above the dead-zone and the curvature signal is not currently in a lobe. Thus, a positive lobe has just started so the positive lobe initialization calculations will follow.

Case 2: $CRV_{thresh} \geqq CRV \geqq -CRV_{thresh}$ and not in a Lobe.

Here, the current curvature values is inside the dead-zone and the curvature signal is not currently in a lobe.

Case 3: $CRV < -CRV_{thresh}$ and not in a Lobe.

Here, the current curvature value is below the dead-zone and the curvature signal is not currently in a lobe. Thus, a negative lobe has just started so the negative lobe initialization calculations will follow.

Case 4: $CRV > CRV_{thresh}$ and in a Positive Lobe.

Here, the current curvature value is above the dead-zone and the curvature signal is in a positive lobe. Thus, the positive lobe continuation calculations will follow.

Case 5: $CRV_{thresh} \geqq CRV \geqq -CRV_{thresh}$ and in a Positive Lobe.

Here, the current curvature value is inside the dead-zone and the curvature signal is in a positive lobe. Thus, a positive lobe has just ended so the positive lobe finalization calculations will follow.

Case 6: $CRV < -CRV_{thresh}$ and in a Positive Lobe.

Here, the current curvature value is below the dead-zone and the curvature signal is currently in a positive lobe. Thus, a positive lobe has just ended and a negative lobe has just started so that both the positive lobe finalization calculations and the negative lobe initialization calculations will follow.

Case 7: $CRV > CRV_{thresh}$ and in a Negative Lobe.

Here, the current curvature value is above the dead-zone and the curvature signal is in a negative lobe. Thus, a negative lobe has just ended and a positive lobe has just started so that both the negative lobe finalization calculations and the positive lobe initialization calculations will follow.

Case 8: $CRV_{thresh} \geqq CRV \geqq -CRV_{thresh}$ and in a Negative Lobe.

Here, the current curvature value is inside the dead-zone and the curvature signal is in a negative lobe. Thus, a lobe has just ended so the negative lobe finalization calculations will follow.

Case 9: $CRV < -CRV_{thresh}$ and in a Negative Lobe.

Here, the current curvature value is below the dead-zone and the curvature signal is in a negative lobe. Thus, the negative lobe continuation calculations will follow.

In one embodiment, hysteresis is used to aid in identifying curvature lobes. After having started a lobe, one embodiment provides that the curvature value cross a threshold value closer to zero in order for the lobe to finish. Thus, hysteresis introduces another threshold value.

Consider next, the metrics for characterizing each lobe according to the present subject matter. In one embodiment, those metrics include the total area of the lobe, the time of the lobe area centroid and the value of the original data at the time of the area centroid. In one embodiment, other metrics or parameters are used to describe the characteristic point, including, for example, the peak curvature in the lobe, the time of the peak curvature, the times of the lobe start or lobe finish, a time of the centroid, a peak, a midpoint, a midpoint at a median value or any other predetermined parameter.

Figure 6:
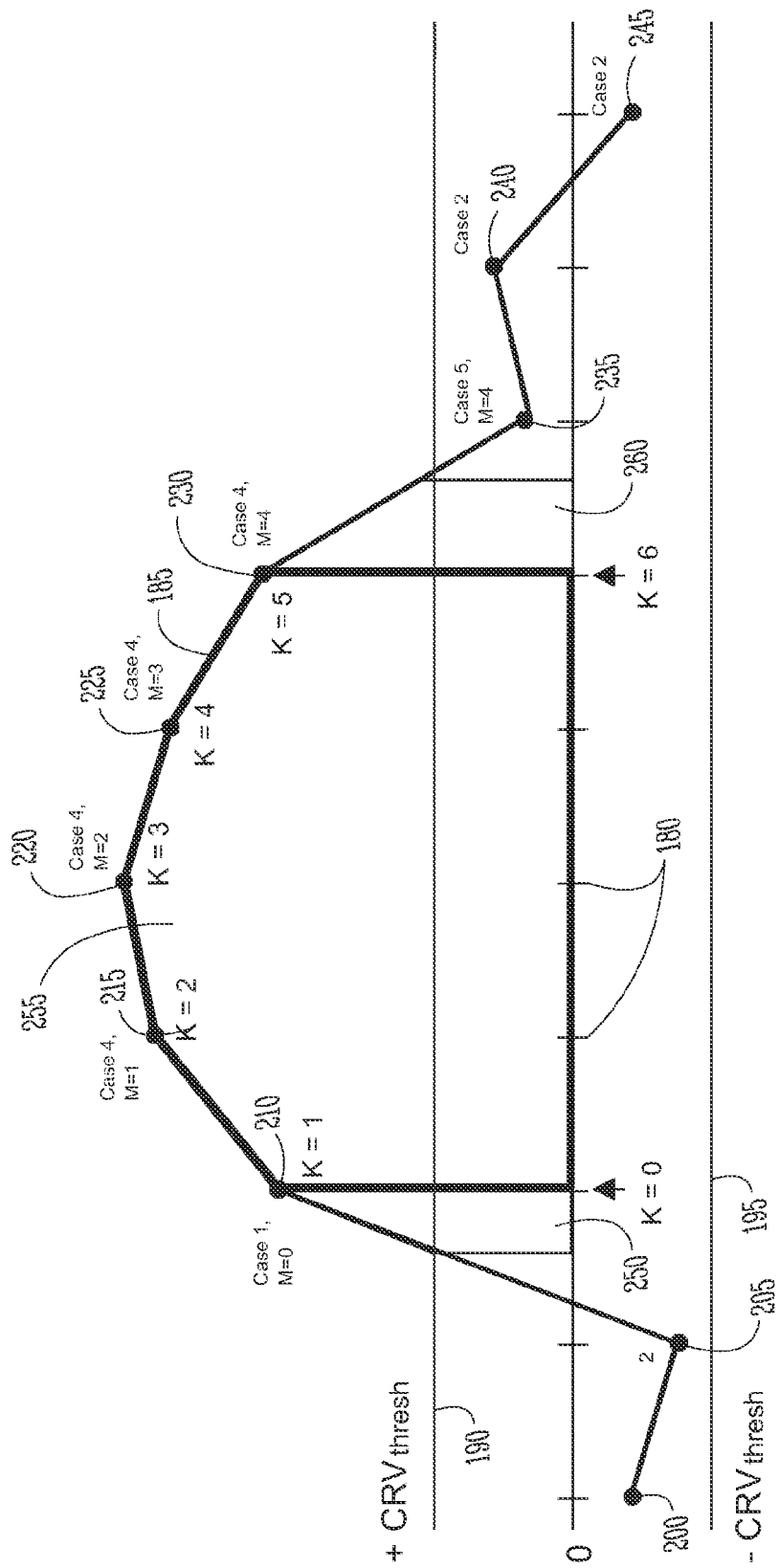
FIG. 6 graphically illustrates a method for determining area under a curvature lobe.

FIG. 6 shows an example of curvature lobe 185 as a series of calculated curvatures at each sample time. Tick marks 180 along the X axis represent the actual samples and thus are separated by $\Delta T$. Zero curvature is shown as the X axis. The threshold curvature values, $+CRV_{thresh}$ 190 and $-CRV_{thresh}$ 195 are shown as horizontal lines above and below the X-axis. Curvature points 200-245 are shown as small solid circles.

As shown in the figure, initial curvature values at curvature points 200 and 205 are within the dead-zone of the threshold curvature values and thus, no lobe is yet established. Curvature point 210 is above the threshold and corresponds to Case 1 described above. The magnitude of initial area 250 is calculated as soon as the lobe is started according to case 1 described above. Upon determining curvature point 215, a contribution to the magnitude of main area 255 is calculated according to case 4 described above. In addition, the magnitude of main area 255 is increased with the determination of curvature points 220, 225, and 230. Upon determining curvature point 235 lying below $+CRV_{thresh}$ 190, the magnitude of final area 260 is calculated for the region below curvature lobe 185 and between curvature point 230 and the intersection with $+CRV_{thresh}$ 190. Curvature points 235, 240 and 245 lie in the dead-zone and do not contribute to an area calculation. The area of curvature lobe 185 is calculated to include the sum of initial area 250, main area 255 and final area 260.

In one embodiment, a value M of a counter is maintained by a processor to monitor sample-by-sample development of a lobe. Initially, it is assumed, the signal will be in the dead-zone and for a sample excursion outside the dead-zone, the value M is reset to zero and incremented with each subsequent point that remains outside the dead-zone. Values for M are illustrated at the different curvature points in FIG. 6.

To find the area under the curvature lobe, the value of M is set to zero and the initial area of a curvature lobe is computed as initial area=$(C_i + CRV_{thresh}) \cdot (C_i - CRV_{thresh})/(C_i - C_{i-1})$ when the lobe is started. For each successive curvature value, the value of M is incremented and the additional area contribution is computed as additional area=$-(M-1) \cdot C_i + M \cdot C_{i-1}$. When the lobe ends, the value of M is not incremented and the final area contribution is computed as final area=$M \cdot C_{i-1}+(C_i+CRV_{thresh}) \cdot (C_i-CRV_{thresh})/(C_i-C_{i-1})$. The sum of the initial, final, and all additional areas may then be multiplied by $\Delta T/2$ to find the area under the curvature lobe.

To find the first moment of the area under the curvature lobe, a similar approach is used. When the initial area of the curvature lobe is computed, the initial moment of the area is also computed as initial moment=$-\{C_1+2\ CRV_{thresh}\} \cdot \gamma^2$ where $\gamma=(CRV_{thresh}-C_{i-1})/(C_i-C_{i-1})$. For each successive curvature value in the lobe, an additional moment contribution is computed using the same M values as for the area computations. This additional moment contribution is computed as additional moment=$\{C_i \cdot (3M-1)+C_{i-1} \cdot (3M-2)\}$. When the lobe ends, a final moment contribution is computed at the same time that the final area is computed. The final moment is computed as final moment=$[CRV_{thresh} \cdot \{3M+2\gamma\}+C_{i-1} \cdot \{3M+\gamma\}] \cdot \gamma$.

The sum of the initial, final, and all additional moments may then be multiplied by $\Delta T^2/6$ to find the first moment of the area under the curvature lobe. The time of the centroid of the curvature lobe area is found by dividing the first moment of the curvature lobe area by the curvature lobe area as time=first moment of area/area. This time is with respect to the time of the curvature point that started the lobe.

For both the area and the first moment of the area, the calculations are constructed in such a way that the contribution of each curvature sample may be summed into a total area or total first moment of the area as the samples are collected. Thus, for all calculations, the factors include the present and previous curvature values, the threshold values, and the counter M. In this manner the area and the time of the centroid of the area are generated as soon as the lobe is ended.

In one embodiment, the present subject matter identifies characteristic points generated from point-by point processing of an input signal. In one embodiment, the characteristic points in the signal are detected and saved into a buffer. In one embodiment, each characteristic point is a set of values including the time of the characteristic point, the value of the input signal at that time, and a value describing the direction and extent of curve in the signal that produced the characteristic point.

In one embodiment, each time a heart beat is detected, the characteristic points for that beat are removed from the buffer and compared to characteristic points of one or more previously stored beat types, thus classifying each beat.

The beat classification process determines if the set of characteristic points describing the present unknown beat matches with the set of characteristic points describing a previously known beat type.

In one embodiment, if a match is found, then a repetition code is stored indicating that the current set of characteristic points is a repeat of a previously stored beat. The repetition code includes a value for the time of the occurrence of the current beat and includes identification of the previously stored beat. In one embodiment, the repetition code identifies the previously stored beat and a code denoting the number of repeated beats and a number corresponding to the time interval between each successive beat.

In one embodiment, a difference code is stored to indicate that the current set of characteristic points differs from the set of characteristic points of a previously stored beat. The difference code includes a value for the time of the occurrence of the current beat and includes identification of the previously stored beat as well as the specific difference(s) from the previously stored beat.

Consider next a method of extracting characteristic points. In one embodiment, characteristic points of an electrocardiogram are extracted using a sampling at 400 Hz. In one embodiment, sampling is performed at 200 Hz. The sampled data is filtered using a 5-point or 3-point running average filter and a 5 least squares regression average-point curvature method to select characteristic points relating to the QRS complex.

For detecting curvatures associated with slower morphologies, sampling is at a slower rate, such as, for example, 50 Hz. An example of a wave having slower morphologies would be the T-wave in an electrocardiogram.

In one embodiment, multiple sampling rates are used for characteristic point extraction.

In one embodiment, dual-rate sampling is performed with sampling at 200 Hz providing fast characteristic points and sampling at 50 Hz providing slow characteristic points and a 3-point running average filter is used.

In one embodiment, curvature is found by using 5-point least squares regression filtering. The coefficients for finding the linear (Bi) and parabolic (Ci) fit-coefficients in the cubic least squares regression to the data at point i are as follows:

| Linear | Parabolic |
| --- | --- |
| $P_{-2} = (1/12) * Rate$ | $Q_{-2} = (10/70) * Rate^2$ |
| $P_{-1} = (-8/12) * Rate$ | $Q_{-1} = (-5/70) * Rate^2$ |
| $P_0 = 0$ | $Q_0 = (-10/70) * Rate^2$ |
| $P_1 = (8/12) * Rate$ | $Q_1 = (-5/70) * Rate^2$ |
| $P_2 = (-1/12) * Rate$ | $Q_2 = (10/70) * Rate^2$ | where Rate is the sampling rate in sample/sec, Bi is the sum of the products of these P least squares regression coefficients multiplied by the 5 corresponding data points centered on i ($D_{i-2}$ to $D_{i+2}$) and Ci is the sum using the Q least squares regression coefficients. Curvature is then computed as:

$$\text{Curvature} = \frac{2 \cdot Ci \cdot W}{[1 + \{Bi \cdot W\}^2]^{3/2}}$$

where W is a constant. Since W appears in conjunction with fit-coefficients Ci or Bi, the value can be incorporated into the computations as a data signal gain such that $D'(i)=W \cdot D(i)$. Then, the curvature expression becomes:

$$\text{Curvature} = \frac{2 \cdot C'i}{[1 + \{B'i\}^2]^{3/2}}$$

where B'i and C'i are found using the D' data points rather than the D data points with the least squares regression coefficients.

The expression for curvature then becomes:

$$Curv' = \text{Curvature} \cdot Gn = \frac{C'i \cdot 2 \cdot Gn}{[1 + \{B'i\}^2]^{3/2}} = \frac{C''i}{[1 + \{B'i\}^2]^{3/2}}$$

where Gn is an arbitrary value which is incorporated (with 2) into C". If the curvature thresholds used for detection of characteristic points is adjusted accordingly, it does not matter whether point-by-point curvature or Gn times the point-by-point curvature is calculated. Incorporating the values $2 \cdot Gn$ into C"i can be accomplished by changing the least squares regression coefficients $Q_{-2}$ through $Q_2$ into new least squares regression coefficients ($Q'_{-2}$ through $Q'_2$) by multiplication with 2Gn. If On is selected as 7/(6 Rate and the term Fn=Rate/12 is incorporated as additional data signal gain, then the least squares regression coefficients become:

| Linear | Parabolic |
|---|---|
| $P''_{-2} = 1$ | $Q''_{-2} = 4$ |
| $P''_{-1} = -8$ | $Q''_{-1} = -2$ |
| $P''_0 = 0$ | $Q''_0 = -4$ |
| $P''_1 = 8$ | $Q''_1 = -2$ |
| $P''_2 = -1$ | $Q''_2 = 4$ | with $D''(i)=2\cdot W\cdot Fn\cdot D(i)$; and with $Ci''=Q''_{-2}\cdot D''(i-2)+Q''_{-1}\cdot D''(i-1)+Q''_0\cdot D''(i)+Q''_{+1}\cdot D''(i+1)+Q''_{+2}\cdot D''(i+2)$; and with $Bi''=P''_{-2}\cdot D''(i-2)+P''_{-1}\cdot D''(i-1)+P''_0\cdot D''(i)+P''_{-1}\cdot D''(i+1)+P''_{-2}\cdot D''(i+2)$.

Note that the coefficients are all powers of 2 (either 0, 1, 2, 4 or 8), thus simplifying hardware or firmware implementation of the present subject matter.

When using use two sample rates for determining characteristic points, the computed curvatures will be different when computed at different rates. Thus, two threshold levels and parallel sets of computations are used. Also, the running average filtering is different with the fast rate filtering using 5 consecutive points while the slow rate filtering uses every fourth point spaced over 16 points.

In one embodiment, the linearity of the least squares regression operation is used. The running average filtering operation are performed at the fit-coefficient level (i.e. the Bs and Cs) rather than the data level. In this embodiment, two filtering operations are performed (one for Bs, one for Cs) at each rate.

In one embodiment, the fast and the slow running average filtering operations are performed in parallel.

To classify the beats for compression purposes, the following implementation is used to determine the characteristic points.

Starting at the time of one sample, the sensing hardware and software of the present subject matter begins acquiring the next sample so that the actual sample reflects the nature of the signal between the last sample and the current sample. At the actual time of the sample, the value of the sample may be ascribed to the time half-way between the current sample and the previous sample. Samples at the slow sample rate apply to the signal two fast sample steps earlier that the actual sample time.

In one embodiment, a circular data buffer is used. Data is acquired at the fast sample rate and used to fill a circular data buffer. Once the timing of a fast or slow characteristic point is determined, the data value for that characteristic point is found from the data stored in the circular buffer. Thus, the data buffer is sized so that the requisite data is still available in the buffer. In one embodiment, the buffer is sized to hold about 500 millisecond of data or 256 data points. In one embodiment, the circular buffer is implemented as a memory array with an index pointer. In one embodiment, the index pointer includes a binary counter and the buffer size is a power of 2.

In one embodiment, running average filtering (RAF) is performed on the input data. In various embodiments, the filtering is provided by a circular buffer or a shift register set. The values in the circular data buffer reflect the fast running average filtering. In one embodiment, a hybrid approach is used where the fast running average filtering is performed and then the data is placed into a circular buffer. In one embodiment, the running average filter includes a shift register approach. The fast sample running average filtering registers are called $DFreg_0$ to $DFreg_{-3}$. In one embodiment, an accumulator $SUM_F$ is also maintained.

When a new fast sample ($D_0$) is obtained, the following operations are carried out:

$$SUM_F = SUM_{Fold} + D_0$$
$$SUM_{Fold} = SUM_F - DFreg_{-1}$$
$$DFreg_{-3} = DFreg_{-2}$$
$$DFreg_{-2} = DFreg_{-1}$$
$$DFreg_{-1} = DFreg_0$$
$$DFreg_0 = D_0$$

The value of $SUM_F$ is the sum of the 3 most recent data points. Thus, circular buffer CircBuf is filled. Next the CircBuf [CBIndex] is set to $SUM_F$, and CBIndex is incremented followed by resetting CBIndex to zero on overflow. The value $SUM_F$ is also loaded into the fast data register set for the least squares regression operation.

On every $4^{th}$ sample at the fast rate, a slow rate sample is obtained as $SLOWVAL=SUM_F+DFreg_{-3}$ and the slow running average filtering operation is performed using the following:

$$SUM_S = SUM_{Sold} + SLOWVAL$$
$$SUM_{Sold} = SUM_S - DSreg_{-1}$$
$$DSreg_{-1} = DSreg_0$$
$$DSreg_0 = SLOWVAL$$

With the above operations, the circular buffer is loaded with the results of the fast running average filtering as the sum of the last 3 samples. The average values are determined by dividing by 5 (or 3). The fast running average filtering average applies to the signal at a time 1.5 time steps back from the time of the current sample.

On each $4^{th}$ sample, SLOWVAL is the sum of the previous 4 fast samples and thus applies to the signal 2 time steps back from the current sample. The result of the slow running average filtering operation is the sum of the last 3 SLOWVAL samples and thus the sum of the last 12 fast samples. Again the average is found by dividing the sum by 12. The slow running average filtering average applies to the signal 6 time steps back from the time current sample.

To perform the least square regression fit (cubic fit) operations, the filtered data point is multiplied by $W\cdot Fn$ where Fn is equal to the sample rate divided by 12. In one embodiment, the slow rate is selected to be ¼ of the fast rate (RATE) and the fast rate and slow rate samples are multiplied by $W\cdot Fn_f=W\cdot RATE/12$ and $W\cdot Fn_s=W\cdot RATE/48=W\cdot Fn_f/4$ respectively. In one embodiment, the value of W is selected such that the product $W\cdot Fn_f$ is a power of 2 which also makes $W\cdot Fn_s$ a power of 2.

In one embodiment, the data used for least squares regression computation is extracted from the circular buffer by manipulating pointers into the buffer to select the correct values. In one embodiment, the data is shifted through a set of 5 registers and the fit computations are performed on the register set.

The fast set of shift registers are called $Freg_0$ through $Freg_{-4}$ and the slow registers are called $Sreg_0$ through $Sreg_{-4}$. The shift operations are:

| | |
|---|---|
| $Freg_{-4} = Freg_{-3}$ | $Sreg_{-4} = Sreg_{-3}$ |
| $Freg_{-3} = Freg_{-2}$ | $Sreg_{-3} = Sreg_{-2}$ |
| $Freg_{-2} = Freg_{-1}$ | $Sreg_{-2} = Sreg_{-1}$ |
| $Freg_{-1} = Freg_{0}$ | $Sreg_{-1} = Sreg_{0}$ | and the data is loaded into the register sets as $Freg_0 = SUM_F \cdot W \cdot Fn_f$ and $Sreg_0 = SUM_S \cdot W \cdot Fn_f/4$.

In one embodiment, the fast register set load/shift/computation operations occur on each sample while the slow register set load/shift/computation operations occur on every $4^{th}$ sample.

In one embodiment, for fast-sampling fit, the least squares regression fit coefficients are obtained by $B''_F = (Freg_{-4} - Freg_0) + 8 \cdot (Freg_{-1} - Freg_{-3})$; and $C''_F = 4 \cdot (Freg_{-4} + Freg_0) - 2 \cdot (Freg_{-1} + Freg_{-3}) - 4 \cdot Freg_{-2}$. The linear and parabolic fit coefficients for the fast sample rate are denoted $B''_F$ and $C''_F$ respectively.

At 200 Hz sampling, the time in the signal at which these cubic least squares regression fit coefficients apply is 3.5 time steps earlier than the time of the current sample. At 200 Hz, 3-point running average filtering is used and the sample again reflects the signal ½ a time step back from the time of the current sample. Furthermore, the running average delay is 1 step, the least square regression delay is 2 steps.

For slow sampling fit, the linear and parabolic fit-coefficients for the slow sample rate are denoted $B''_S$ and $C''_S$ respectively and are found from the slow register set as $B''_S = (Sreg_{-4} - Sreg_0) + 8 \cdot (Sreg_{-1} - Sreg_{-3})$; and $C''_S = 4 \cdot (Sreg_{-4} + Sreg_0) - 2 \cdot (Sreg_{-1} + Sreg_{-3}) - 4 \cdot Sreg_{-2}$.

The mechanics of filtering, regression, and curvature calculation are the same as the fast sample rate. The time in the signal at which these slow cubic least squares coefficient fits apply is 3½ slow (14 fast) time steps earlier than the time of the current sample. Each slow sample is the sum (or average) of the 4 recent fast samples. Thus, when a slow sample occurs (i.e. on each $4^{th}$ fast sample), the slow sample has the same time as the concurrent fast sample time. However, the slow sample applies to the signal ½ slow time steps (i.e. 2 fast time steps) earlier than the current slow sample time. The 3-point running average delay is 1 slow (4 fast) samples and the least squares regression delay is 2 slow (8 fast) samples for a total of 3½ slow (14 fast) sample time steps.

In one embodiment, a fast curvature value is computed for each current fast sample from the fast linear ($B_f''$) and parabolic ($C_f''$) least square regression fit coefficients. In one embodiment, a slow curvature value is computed for each current slow sample from the slow linear ($B_s''$) and parabolic ($C_s''$) least square regression fit coefficients.

In one embodiment these curvatures are computed as point curvatures as Curvature=$C''/(1+B'')^{3/2}$ where $C''$ and $B''$ are the current fast or slow fit coefficient.

In one embodiment, these curvatures are computed as average-point curvatures as $$\text{Curvature} = \frac{1}{(B'' - B_0'')^2}$$

$$\left\{ \frac{C_0'' B''^2 - C'' B'' B_0'' - C'' + C_0''}{(B''^2 + 1)^{1/2}} + \frac{C'' B_0''^2 - C_0'' B_0'' B'' + C'' - C_0''}{(B_0^2 + 1)^{1/2}} \right\},$$

$$B'' \neq B_0''$$

$$Cavg_i = \frac{1}{2} \cdot \frac{C'' + C_0''}{(B''^2 + 1)^{3/2}}, B'' = B_0''$$

where $C''$ and $B''$ are the current fast or slow fit coefficients and $C_0''$ and $B_0''$ are the previous value for these same coefficients.

In one embodiment, running average filtering reduces curvature noise relative to the signal content of fast curvature signals. An electrocardiogram signal typically takes relatively large excursions away from zero curvature at the times of fast turns in the signal. However, when the fast turns are less severe, the curvature signal does not move as far away from zero and curvature noise can prematurely end the curve lobe. The result is that one small curvature lobe is broken into two or more even smaller lobes. Thus, in one embodiment, the curvature noise relative to the signal content is reduced, for fast curvature signals, by running average filtering.

Filtering of the input signal does not achieve the same effect as filtering the actual curvature signals. In one embodiment, 3-point running average filtering is applied to the fast curvature values.

In one embodiment, fast curvature values are computed as average point curvature and 3 point running average filtering of the curvatures so that the fast curvature value computed when the current sample is taken applies to a time in the input signal that is 5 time steps earlier than the current sample.

In one embodiment, slow curvature values are computed at ¼ the fast sample rate and are computed as average-point curvatures so that when the every fourth fast sample is taken, slow curvature is computed and it applies at a time in the input signal that is 4 slow (16 fast) time steps earlier than the current sample.

In one embodiment, the detection of a curvature-lobe and characteristic points entails both fast and slow characteristic point detection performed in parallel. In one embodiment, separate curvature thresholds and curvature area thresholds are used for the fast and slow operations.

In one embodiment, a curvature lobe is ended when the curvature signal crosses the same threshold used to start the lobe but in the opposite direction of the crossing that started the lobe. In one embodiment, a hysteresis is used so that a curvature lobe is ended when the curvature signal crosses a threshold that is smaller (i.e. closer to zero) than the threshold used to start the lobe but in the opposite direction of the crossing that started the lobe. In one embodiment, a curvature lobe is ended when the curvature signal crosses zero as the hysteresis value.

In one embodiment, the value of W is selected according to the following procedure. Select an approximate range for W from the following analysis. At a 200 Hz sampling rate, the QRS takes approximately 5 samples. The signal at the peak is approximated by 128. If the QRS were to be approximated (in curvature-space) as a semicircle arching from 0 to the peak then back to 0 in 5 points, then the radius of that semicircle would be 0.01 sec and the peak would have a value of 0.01. Thus, the value of W would be the one that, when multiplied, the peak (128) would have the value of 0.01, i.e. W=0.01/128=0.000078. In one embodiment, W=0.000122=1/8192 which is a power of 2.

Consider selection of curvature threshold values for characteristic point detection. Thresholds, in one embodiment, reduce or eliminate the noise characteristic points and computational burden. This noise is the natural results of the curvature signal hovering around zero (or some other value) when the raw signal does not otherwise have characteristic turnings.

In one embodiment, for a curvature lobe to be detected, the point-wise curvature falls outside of a dead-band formed by the threshold values on either side of zero. Reducing this threshold towards zero increases the number of curvature lobes that are detected and increases the computational burden. In one embodiment, a threshold value is selected by using approximately a 1 minute epoch of the input signal to make a histogram of the fast curvature values computed at each sample time. The threshold value is selected as one which corresponds to 20% of the peak. This value is then used as the threshold for both the fast curvature and slow curvature feature selection process.

In one embodiment, the noise lobes are removed by requiring that a detected lobe must exceed a critical area limit. The noise lobes have generally small areas while the real lobes associated with characteristic turns in the signal usually have substantial areas. In one embodiment, the area limit of 0.1 is used.

In one embodiment, different values are used for the fast curvature and slow curvature area thresholds. In one embodiment, these thresholds are pre-selected. In one embodiment, the thresholds are adapted to patient signals. Adapting the thresholds may occur once in a learning session or may occur periodically. In one embodiment, the thresholds are adapted by using the number of beats occurring in a one minute epoch to set the gain and curvature thresholds and selecting a desired number of fast and slow characteristic points to find for these beats.

For example, in one embodiment, 5 fast characteristic points per beat and 8 slow characteristic point per beat are used as targets. The area thresholds are then adjusted until these target numbers of characteristic points are found. In one embodiment, a lower area limit of 0.1 is used.

Signal Compression

In one embodiment of the present subject matter, data corresponding to the sampled signal is stored in the form of characteristic points. For example, rather than storing all data points from a sampled input signal, one embodiment provides that the characteristic points are stored. Each characteristic point, in one embodiment, includes a time of occurrence of that characteristic point and the amplitude of the input signal at that time. In one embodiment, each characteristic point includes data as a function of the size of the lobe at that time.

In one embodiment, a minimum absolute value of a size of a characteristic point is established as a threshold value. In such a case, a characteristic point is discarded or not stored if the absolute value of the size is less than a minimum absolute value and stored if the value is greater than the minimum absolute value. For example, in one embodiment, a minimum size of 0.1 is established.

In one embodiment, the threshold value is stored in a memory accessible to a processor of the present subject matter. In one embodiment, the threshold value is a fixed value. In one embodiment, the threshold value is a variable and is adjusted manually or automatically. In one embodiment, the threshold value is varied as a function of the input signal or other measured parameter. For example, in one embodiment where the input signal is an electrocardiogram, the threshold value is varied as a function of the beat frequency.

Other compression systems are also contemplated for use with repetitive signals. For example, in one embodiment where the input signal is an electrocardiogram, a library of beat types are classified and stored in memory. Each beat is represented by a series of characteristic points and using methods described herein, the set of characteristic points are assembled in a group or cluster. In one embodiment, subsequent beats, having a relationship with the previously stored group of characteristic points, are stored by referencing the previously stored beat group.

Figure 7:
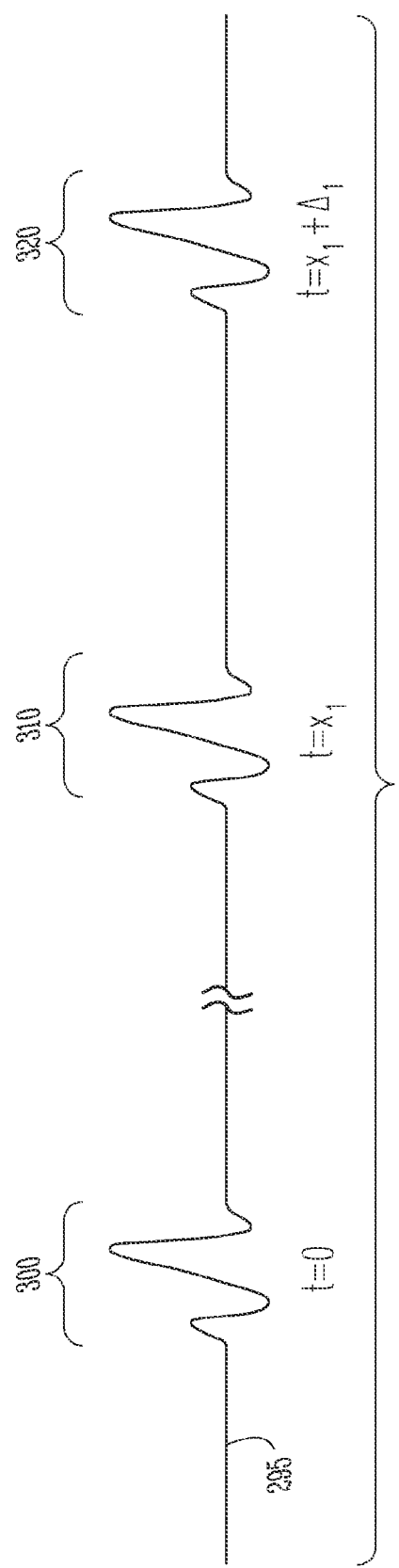
FIG. 7 illustrates tabulated data for compressing as a function of a repeated cluster of characteristic points.

In one embodiment, the relationship is one in which the subsequent beat matches a previously stored beat. FIG. 7 illustrates tabulated data for compressing as a function of a repeated cluster of characteristic points. In the figure, electrocardiogram 295 includes beats 300, 310 and 320. In the figure, beat 300 is indicated to have occurred at time 0, beat 310 at time $x_1$ and beat 320 at time $x_1 + \Delta_1$. Table 1 identifies cluster 305, cluster 315 and cluster 325, associated with beat 300, beat 310 and beat 320, respectively. Each cluster includes a set of characteristic points labeled CP1-CP7 with each characteristic point having an associated time, amplitude and size. In memory, the characteristic points of cluster 305 are associated with a particular beat type occurring at a specified time.

TABLE 1

|     | Time | Amp  | Size | Time         | Amp  | Size | Time                    | Amp  | Size |
|-----|------|------|------|--------------|------|------|-------------------------|------|------|
| CP1 | -126 | 47   | -337 | $x_1 + -126$ | 47   | -337 | $x_1 + \Delta_1 + -126$ | 47   | -337 |
| CP2 | 20   | -613 | 856  | $x_1 + 20$   | -613 | 856  | $x_1 + \Delta_1 + 20$   | -613 | 856  |
| CP3 | 108  | 752  | -817 | $x_1 + 108$  | 752  | 817  | $x_1 + \Delta_1 + 108$  | 752  | 817  |
| CP4 | 233  | 229  | 226  | $x_1 + 233$  | 229  | 226  | $x_1 + \Delta_1 + 233$  | 229  | 226  |
| CP5 | 328  | 65   | 206  | $x_1 + 328$  | 65   | 206  | $x_1 + \Delta_1 + 328$  | 65   | 206  |
| CP6 | 373  | 94   | -382 | $x_1 + 373$  | 94   | -382 | $x_1 + \Delta_1 + 373$  | 94   | -382 |
| CP7 | 474  | -405 | 479  | $x_1 + 474$  | -405 | 479  | $x_1 + \Delta_1 + 474$  | -405 | 479  |
|     | Cluster 305 |  |  | Cluster 315 |  |  | Cluster 325 |  |  |

As shown in the figure, beat 310 and beat 320 are found to be a match with beat 300. Criteria for determining a suitable match between beats entails, among other things, establishing alignment between the beats and comparing relevant features.

In one embodiment, a repetition marker is stored in memory to indicate the occurrence of beat 310 and beat 320. The repetition marker, in one embodiment, includes identification of beat 300. The repetition marker, in one embodiment, includes timing information to denote that beat 310 occurred at time $x_1$ and that beat 320 occurred at time $x_1 + \Delta_1$. In one embodiment, the repetition marker indicates that an interval of time between beat 310 and beat 320 is $\Delta_1$.

In one embodiment, a series of matched repeated beats is stored in memory as a duplicate of a previously stored beat along with a uniform interval of time between consecutive beats.

Figure 8:
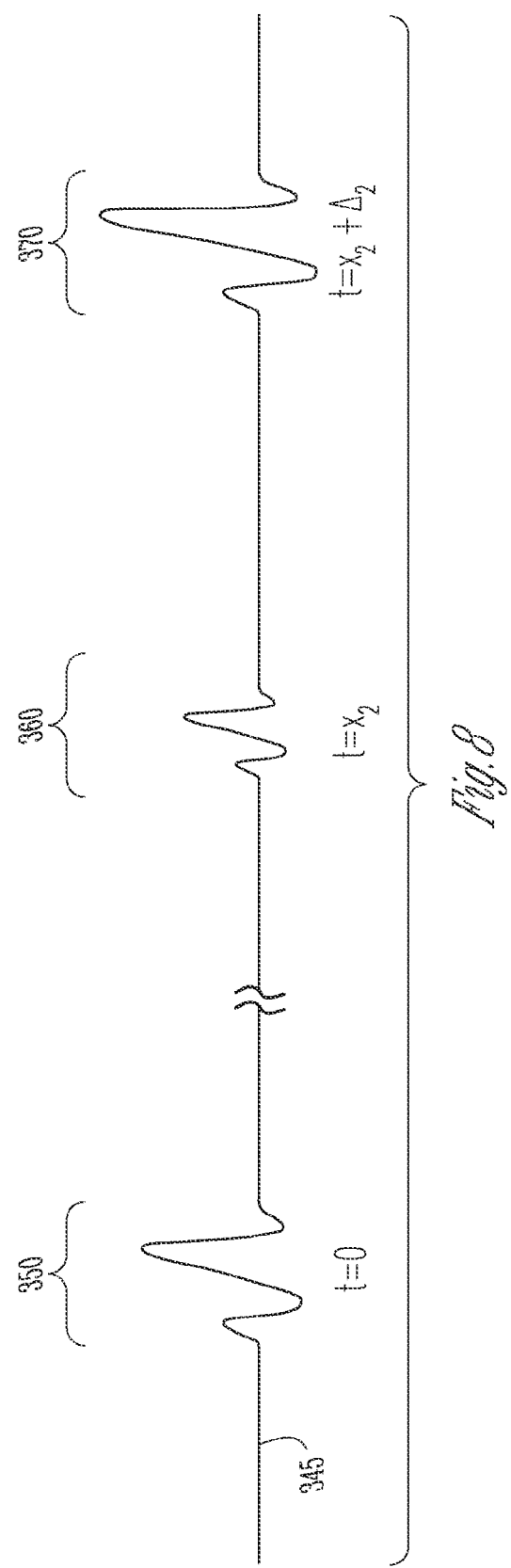
FIG. 8 illustrates tabulated data for compressing as a function of a cluster of characteristic points that differs from a previous cluster of characteristic points.

FIG. 8 illustrates exemplary electrocardiogram 345 having beat 350, 360 and 370, each of which differ. Table 2 identifies cluster 355, cluster 365 and cluster 375, associated with beat 350, beat 360 and beat 370, respectively. Each cluster includes a set of characteristic points labeled CP1-CP7 with each characteristic point having an associated time, amplitude and size. In this example, beat 350 occurred at time t=0 and has a cluster of characteristic points CP1-CP7 as shown in cluster 355. Beat 360 occurred at time $t=x_2$ and has a cluster of characteristic points as shown in cluster 365. Beat 370 occurred at time $t=x_2+\Delta_2$ and has a cluster of characteristic points as shown in cluster 375. The entries in cluster 365 for CP7 differ from those of CP7 of cluster 355. The entries in cluster 375 indicate that the size of each characteristic point is different from the size of each characteristic point in cluster 355. In one embodiment, beat 360 and beat 370 are stored in memory using difference markers. In one embodiment, the difference marker includes identification of beat 350. The difference marker, in one embodiment, includes timing information to denote that beat 360 occurred at time t=$x_2$ and that beat 370 occurred at time $x_2+\Delta_2$. The difference marker, in one embodiment, indicates the differences in characteristic point CP7 of cluster 365 relative to that of cluster 355. For example, according to one embodiment and with respect to the figure and Table 2, the difference marker for cluster 365 indicates $CP7_A$=51; 25; −58. The difference marker, in one embodiment, indicates the differences in size of each characteristic point of cluster 375 relative to that of cluster 355. For example, according to one embodiment and with respect to the figure and Table 2, the difference marker for cluster 375 indicates $SIZE_A$=+10; −30; +40; 0; 0; −30; 90. Other encoding schemes are also contemplated for both the difference marker as well as the repetition marker.

TABLE 2

|  | Time | Amp | Size | Time | Amp | Size | Time | Amp | Size |
|---|---|---|---|---|---|---|---|---|---|
| CP1 | −126 | 47 | −337 | $x_2 + -126$ | 47 | −337 | $x_2 + \Delta_2 + -126$ | 47 | −327 |
| CP2 | 20 | −613 | 856 | $x_2 + 20$ | −613 | 856 | $x_2 + \Delta_2 + 20$ | −613 | 826 |
| CP3 | 108 | 752 | −817 | $x_2 + 108$ | 752 | −817 | $x_2 + \Delta_2 + 108$ | 752 | −777 |
| CP4 | 233 | 229 | 226 | $x_2 + 233$ | 229 | 226 | $x_2 + \Delta_2 + 233$ | 229 | 226 |
| CP5 | 328 | 65 | 206 | $x_2 + 328$ | 65 | 206 | $x_2 + \Delta_2 + 328$ | 65 | 206 |
| CP6 | 373 | 94 | −382 | $x_2 + 373$ | 94 | −382 | $x_2 + \Delta_2 + 373$ | 94 | −412 |
| CP7 | 474 | −405 | 479 | $x_2 + 525$ | −380 | 421 | $x_2 + \Delta_2 + 474$ | −380 | 569 |
|  | Cluster 355 | | | Cluster 365 | | | Cluster 375 | | |

Figure 9:
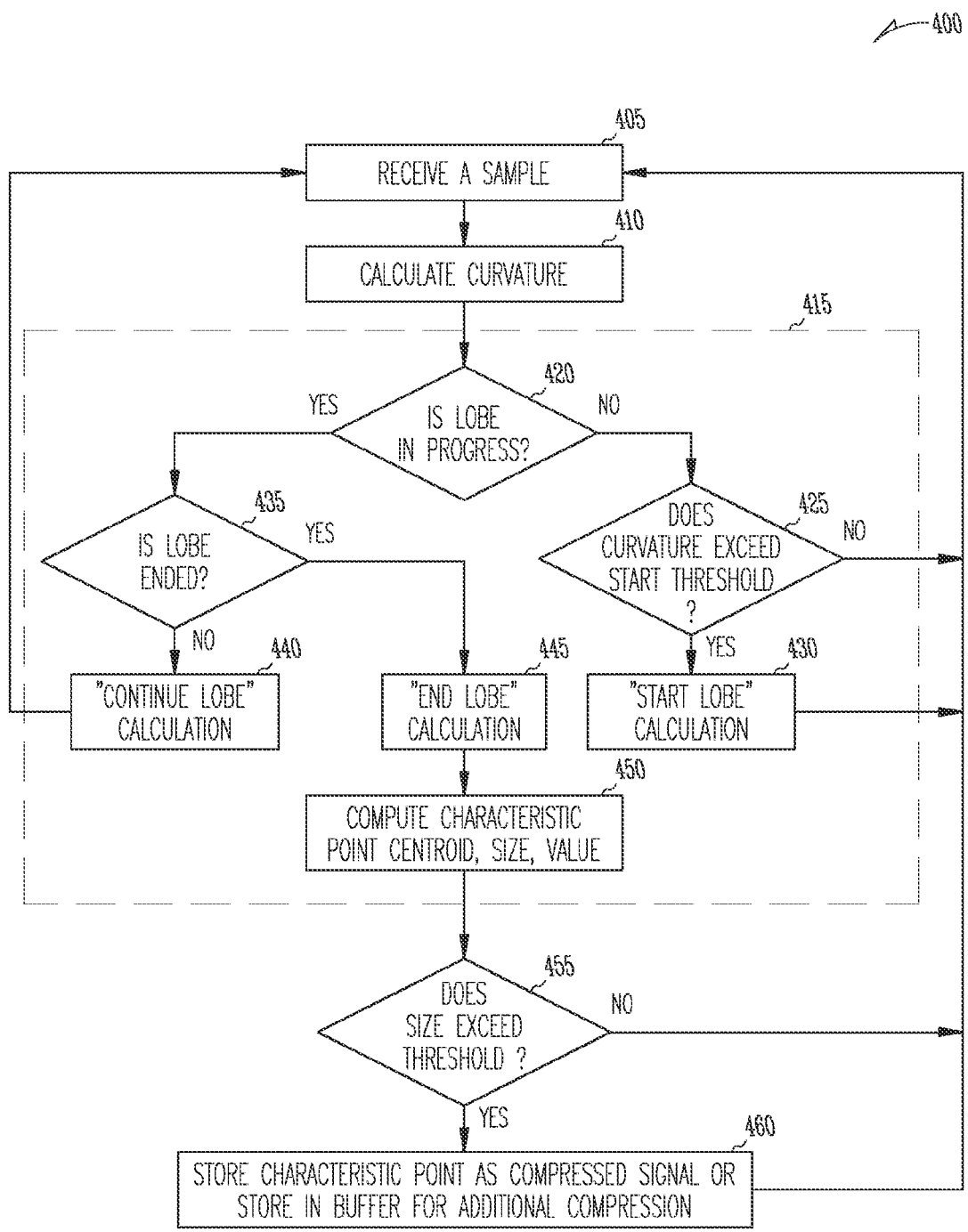
FIG. 9 illustrates a method to determine a characteristic point according to one embodiment of the present subject matter.

FIG. 9 illustrates method 400 according to one embodiment of the present subject matter. At 405, a sample point is received. The sample point corresponds to data from a signal to be compressed. In one embodiment, a sample series is stored in memory and receiving the sample point entails accessing the memory. At 410, a value for the curvature is calculated for the sample point. Curvature is a function of the first and second derivatives at the sample point, as described elsewhere in this document. At 415, the series of curvatures values are processed to identify lobes above or below zero where each lobe corresponds to a single characteristic point. In one embodiment, the calculations to determine each characteristic point value is performed as the series of curvature values are processed as described elsewhere in this document. At 420, an inquiry is made to determine if a lobe is already started but not yet finished. If a lobe is not in progress, at 425 an inquiry is made to determine if the curvature sample is large enough to start a lobe and if so, at 430 the calculations for starting a lobe are made. If at 420 a lobe is in progress, at 435 an inquiry is made to determine if the curvature value is such that the current lobe has ended. If not, at 440 the calculations for the lobe are continued. If the lobe has ended, at 445 the calculations to end the lobe are made and at 450 the characteristic point values are found. At 455, an inquiry is made to determine if the characteristic point is large enough to be saved and if so, at 460 the characteristic point is saved either as the compressed signal or stored in a buffer for additional compression. It will be recognized that the above sequence of steps entails identifying a characteristic point.

Figure 10:
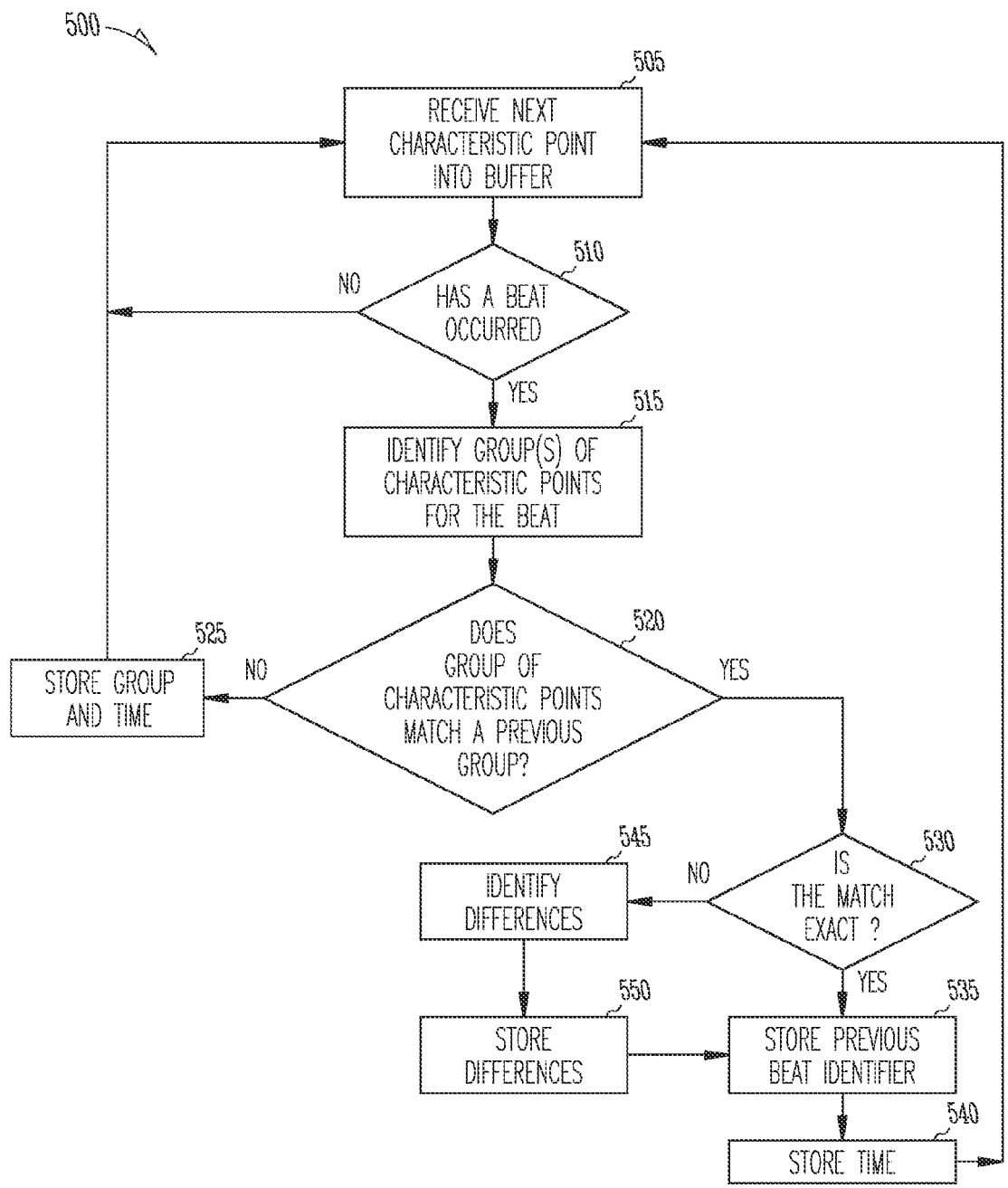
FIG. 10 illustrates a method to find and store repeated groups of characteristic points according to one embodiment of the present subject matter.

FIG. 10 illustrates method 500 for additional compression according to one embodiment of the present subject matter. At 505, the next characteristic point is received and placed into a buffer. At 510, an inquiry is made to determine if a beat has occurred in the signal to be compressed. In one embodiment this determination is made from the characteristic points in the buffer. In one embodiment this determination is made from other processing of the signal to be compressed. In one embodiment, the beat is a periodic component of the signal to be compressed. In one embodiment, the signal is a cardiac signal and the beat is a heartbeat.

If a beat has occurred, at 515 one or more groups of characteristic points in the buffer are identified. In one embodiment, groups are identified based on the timing of characteristic points relative to the times of the current and/or previous beats. In one embodiment, the group includes all members in the buffer since the previous beat. In one embodiment, the groups are formed using the values of the characteristic points stored in the buffer.

At 520, an inquiry is made for each identified group of characteristic points to determine if the group of characteristic points matches with a previously stored group. If the group does not match, then at 525 the group and time are stored in the compressed signal and processing returns to receiving the next characteristic point. If the group does match, then at 530, an inquiry is made to determine if the match is exact. If the match is exact, then at 535 an identifier for the matched group is stored in the compressed signal and at 540, the time for the group is stored in the compressed signal and processing returns to receiving the next characteristic point. If the match is not exact, then at 545, the differences from the matched group are found and at 550 the differences are stored and then at 535 and 540 the matched beat identifier and time are stored and processing returns to receiving the next characteristic point.

In one embodiment, a library of previously stored groups is compared with each subsequent group to determine if a match exists. In one embodiment, a library of previously stored groups is compared with each subsequent group to identify differences. In one embodiment, both differences and matches are identified.

Reconstruction

A reconstruction of the input signal can be generated as a function of the stored characteristic points. In one embodiment, for example, the input signal is modeled as a series of straight line segments connecting characteristic points in chronological order. In this embodiment, the area, or size, of the characteristic point is ignored or discarded and a plot is created using the time and amplitude.

In one embodiment, a polynomial function is fitted to a series of characteristic points to reconstruct the input signal. In various embodiments, the polynomial function includes a parabolic function or a cubic spline function. In one embodiment, the area of the lobe is used in reconstructing the signal. In one embodiment, the start time for each lobe is used in reconstructing the signal. Other criteria can also be used for reconstructing the signal. For example, the area, the end time of the lobe, a peak value, or other parameter describing the lobe is stored and later used to reconstruct the signal.

Exemplary Device

In one embodiment, the present subject matter includes circuitry, hardware and software for implantation in a body. In one embodiment, the present subject matter is adapted for use external to a body.

Figure 11:
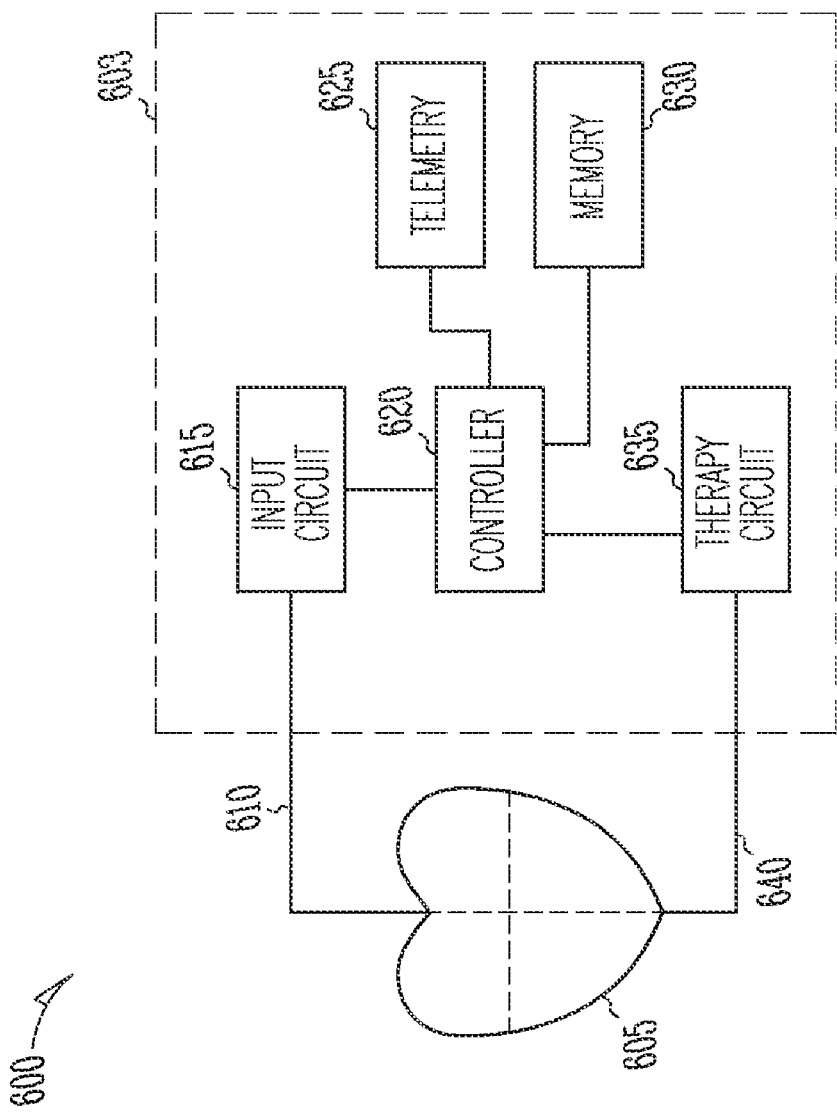
FIG. 11 illustrates a block diagram of an implantable device according to one embodiment of the present subject matter.

FIG. 11 includes a diagram of one embodiment of portions of cardiac rhythm management system 600 according to the present subject matter. As illustrated, system 600 includes unit 603, lead 610 and lead 640, each of which are coupled to heart 605. In various embodiments, unit 603 includes an implantable unit and operates as a pacemaker, a CRT device, heart failure or cardiac resynchronization device, a cardioverter/defibrillator, a pacer/defibrillator and a drug delivery device. In the figure, unit 603 senses cardiac activities from heart 605 and delivers therapy to heart 605 according to programming and circuitry of unit 603. Leads 610 and 640 provide electrical connections between unit 603 and heart 605 and each includes an electrode adapted to be disposed in or about heart 605. Lead 610 is coupled to input circuit 615 and provides an electrical signal sensed from cardiac activity of heart 605. Lead 640 provides therapy to heart 605 as a function of a signal received from therapy circuit 635.

In one embodiment, unit 603 includes input circuit 615, controller 620, telemetry circuit 625, memory 630 and therapy circuit 635. Input circuit 615 is coupled to lead 610 and receives an analog signal based on cardiac activity of heart 605. In one embodiment, input circuit 615 includes an analog-to-digital converter.

In one embodiment, controller 620 includes a processor and programming to implement a method as described herein. In one embodiment, controller 620 includes a circuit to control therapy circuit 635 and telemetry circuit 625.

Memory 630 is coupled to controller 620 and provides storage for compressed and uncompressed data. In one embodiment, the input signal is sampled and stored in memory 630 and at a later time, the data is accessed, compressed and stored again in memory 630. In one embodiment, programming executing on a processor of controller 620 is stored in memory 630.

In one embodiment, controller 620 determines what therapy is to be delivered by therapy circuit 635 to heart 605 using lead 640.

In one embodiment, controller 620 determines what data is to be communicated using telemetry circuit 625. Telemetry circuit 625, in various embodiments is adapted to provide wired or wireless telemetry.

In one embodiment, controller 620 includes a comparator which generates an output based on a comparison of an input signal and a reference signal. Exemplary comparisons include determining if the lobe is making a positive or negative excursion from a baseline. In one embodiment, an exemplary comparison includes determining if the curvature series lobe is greater or less than a dead-zone threshold. In one embodiment, an exemplary comparison includes comparing the curvature signal with a hysteresis value of a threshold.

In the figure, two leads are shown coupled to heart 605. In one embodiment, a single lead provides both sensing and therapy for heart 605.

Alternative Embodiments

Variations of the above embodiments are also contemplated. For example, in one embodiment, the present subject matter is adapted to compress data that is received from an implanted medical device. In one embodiment, the present subject matter is used to compress templates and waveforms for storage in an implanted medical device.

In one embodiment, the present subject matter is used to compress an arbitrary waveform or signal. In addition to compressing voltage as a function of time, other parameters are also candidates for compression. For example, in various embodiments, a temperature signal, a sensor signal, an accelerometer, an impedance measurement or other varying signal is compressed using the present subject matter. In various embodiments, a digital or analog signal is compressed using the present subject matter.

In one embodiment, a slowly changing signal, such as temperature as a function of time, QRS width as a function of time or QT as a function of time, is compressed using the present subject matter.

The characteristic points may result from a fast sampling rate or a slow sampling rate. In one embodiment, a number of sampling rates greater than two are provided, wherein a sampling rate is stored with each characteristic point. In one embodiment, the threshold values are adjusted based on the sampling rate.

In one embodiment, the time resolution for sampling is adjusted to achieve a desired compression ratio. In one embodiment, the signal amplitude resolution is adjusted to achieve a desired compression ratio. For example, with a slowly varying input signal, a lower resolution of the signal amplitude yields satisfactory results. In one embodiment, data denoting the time resolution and the signal amplitude resolution is stored with each characteristic point.

In one embodiment, the present subject matter includes a data storage medium, such as a computer disk, with programming to execute a method as described herein.

In one embodiment, the present subject matter is implemented in dedicated circuitry to perform a method described herein without use of a microprocessor and programming. The circuitry may include hardwired analog or digital circuitry including, for example, operational amplifiers or logical gates.

In one embodiment, the present subject matter stores a group of characteristic points associated with a particular pattern of excursions in the input signal and stores the group in memory. When the pattern occurs at a later time in the input signal, as identified by a subsequent group of characteristic points, a repetition, or similarity, marker is stored in memory. When a different pattern occurs at a later time in the input signal, as identified by a subsequent group of characteristic points, a difference marker is stored in memory. In one embodiment, the particular pattern includes one or more heart beats in an electrocardiogram. In one embodiment, the particular pattern includes, for example, a series of five regular heart beats followed by a spike.

In one embodiment, the present subject matter includes a circuit to receive a sampled electrocardiogram signal and generate a plurality of characteristic points. As a function of the archival history of characteristic points stored in a memory, the present subject matter, in one embodiment, is programmed to deliver therapy, manage therapy, or adjust therapy. For example, the historical record of the cardiac signal, stored as a sequence of characteristic points, may reveal that a particular therapy regimen is appropriate for a particular patient. The long term memory capacity of the present subject matter enables storage of data for extended periods of time.

CONCLUSION

The above description is intended to be illustrative, and not restrictive. Many other embodiments will be apparent to those of skill in the art upon reviewing the above description.

What is claimed is:

1. A system comprising:
   an input circuit adapted to receive a sampled signal;
   a controller coupled to the input circuit and programmed to:
      generate a curvature series as a function of the sampled signal, the curvature series corresponding to a curvature signal;
      identify lobes in the curvature series, the lobes each corresponding to a portion of the curvature signal starting when the curvature signal crosses a first threshold in one direction and ending when the curvature signal crosses a second threshold in an opposite direction;
      calculate an area for each lobe of the identified lobes between the portion of the curvature signal corresponding to the each lobe and a baseline;
      identify a parameter of the each lobe if the area of the each lobe is greater than a predetermined value; and
      generate a characteristic point including a time of the parameter and an amplitude corresponding to the time of the parameter; and
   a memory coupled to the curvature series generator and adapted to store the characteristic points generated by the controller.

2. The system of claim 1 further comprising a cardiac electrode, and wherein the input circuit is coupled to a cardiac electrode.

3. The system of claim 1 wherein the controller is programmed to identify a centroid of a lobe of the identified lobes.

4. The system of claim 1 wherein the controller is programmed to identify a start time of a lobe of the identified lobes.

5. The system of claim 1 wherein the controller is programmed to identify an end time of a lobe of the identified lobes.

6. The system of claim 1 wherein the controller includes a processor.

7. The system of claim 1 further including a telemetry circuit adapted to wirelessly communicate the plurality of characteristic points stored in the memory.

8. The system of claim 1 wherein the characteristic point includes the area of the each lobe.

9. An implantable medical device, comprising:
   an input circuit to receive a sampled cardiac signal;
   a controller coupled to the input circuit wherein the controller is programmed to:
      generate a curvature series as a function of the sampled signal, the curvature series corresponding to a curvature signal;
      identify lobes in the curvature series, the lobes each corresponding to a portion of the curvature signal starting when the curvature signal crosses a first threshold in one direction and ending when the curvature signal crosses a second threshold in an opposite direction;
      calculate an area for each lobe of the identified lobes between the portion of the curvature signal corresponding to the each lobe and a baseline; and
      generate a plurality of characteristic points as a function of the curvature series, each characteristic point of the plurality of characteristic points associated with a lobe of the identified lobes that has an area greater than a predetermined value and including a time component corresponding to a time of occurrence of the lobe and an amplitude component of the sampled cardiac signal at the time of the occurrence; and
   a memory coupled to the controller and adapted to store each characteristic point of the plurality of characteristic points.

10. The device of claim 9 wherein the controller is programmed to generate a first data set corresponding to a first group of characteristic points and the memory is adapted to store the first data set.

11. The device of claim 10 wherein the controller is programmed to generate a second data set and a repetition marker corresponding to a second data set wherein the second data set includes a second group of characteristic points that substantially match the first group of characteristic points and wherein the repetition marker identifies the first data set.

12. The device of claim 11 wherein the controller is programmed to determine a time value as a function of a time of occurrence of the second data set, the time value associated with the repetition marker.

13. The device of claim 10 wherein the controller is programmed to generate a difference marker corresponding to a second data set wherein the second data set includes a second group of characteristic points that differs from the first group of characteristic points and wherein the difference marker identities the first data set.

14. The device of claim 13 wherein the controller is programmed to generate difference data associated with the difference marker, the difference data corresponding to a difference between the first data set and the second data set.

15. The device of claim 9 wherein the controller includes a processor and wherein the memory includes executable instructions accessible to the processor.

16. The device of claim 9 wherein the controller includes hardwired circuitry.

17. The device of claim 9 wherein the controller includes a filter adapted to generate a running average of the sampled cardiac signal.

18. The device of claim 9 wherein the controller includes a comparator.

19. The device of claim 18, wherein the comparator is adapted to determine if the each lobe is making a positive or negative excursion from the baseline.

20. The device of claim 9 wherein the time of occurrence of the lobe includes a time of occurrence of a centroid of the lobe.

21. The device of claim 9 further comprising a therapy circuit coupled to the controller, and wherein the controller includes a circuit to control the therapy circuit.

* * * * *